US005894338A

United States Patent [19]
Miehle et al.

[11] Patent Number: 5,894,338
[45] Date of Patent: Apr. 13, 1999

[54] SYSTEM AND METHOD FOR DIAGNOSING VISION DISORDERS

[75] Inventors: Mark R. Miehle, Del Mar, Calif.; Keith Ignotz, Duluth, Ga.; Ronald Banfiel, Flagstaff, Ariz.; Nathan Morgan, San Diego; Bryan Moore, Carlsbad, both of Calif.

[73] Assignee: VISMED, San Diego, Calif.

[21] Appl. No.: 08/937,375

[22] Filed: Sep. 25, 1997

[51] Int. Cl.$^6$ .................................................. A61B 3/00
[52] U.S. Cl. ...................................................... 351/206
[58] Field of Search ................................... 351/200, 205, 351/206, 207, 208, 246

[56] References Cited

U.S. PATENT DOCUMENTS

| | | | |
|---|---|---|---|
| 4,349,250 | 9/1982 | Gelius | 351/32 |
| 4,715,703 | 12/1987 | Cornsweet et al. | 351/206 |
| 5,565,949 | 10/1996 | Kasha, Jr. | 351/224 |
| 5,677,750 | 10/1997 | Qi | 351/206 |

OTHER PUBLICATIONS

Jonathan D. Trobe, et al., "The Visual Fields Manual, A Practical Guide to Testing and Interpretation," pp. 4, 7, 9, 21, 33, 42 and 112.

Elliot B. Werner, "Manual of Visual Fields," pp. 3, 10, 15 and 118.

Thomas L. Lewis, et al., "Primary Care of the Glaucomas," p. 376.

Thomas D. Duane, "Clinical Opthalmology, The Retina Glaucoma," vol. 3, 1984, Chapter 3, pp. 1 & 14.

Primary Examiner—George Manuel
Attorney, Agent, or Firm—Fleshner & Kim

[57] ABSTRACT

A device and method for comparing and correlating two or more disparate types of test data allows a doctor or technician to easily diagnose a condition or defect. A device or method embodying the invention can be used for diagnosing vision disorders by correlating visual sensitivity or acuity data to images or data corresponding to biological structures responsible for vision. Such a method allows a doctor to easily identify defects or conditions of a biological structure that causes a loss of vision. For instance, perimetry data which is indicative of visual sensitivity may be superimposed onto a fundus image of an eye to create a combined presentation of the data. In the combined presentation, the perimetry data overlies corresponding physical structures shown in the fundus image that give rise to the indicated optical sensitivities. The biological structure data may include an image of an eye, or an image of an optic nerve or a portion a brain responsible for processing optical data. The optical sensitivity data can be in the form of numerals indicative of optical sensitivity, isopter lines, or other types of patterns or symbols indicative of optical sensitivity. In one embodiment of the invention, optical sensitivity data and biological structure data may be stored in multiple data layers, and the data layers can be compared to one another to identify pattern matches between data layers. Similar methods can be used to compare and correlate any two or more disparate types of test data.

48 Claims, 10 Drawing Sheets

FIG. 3

RIGHT          LEFT

SYSTEM AND METHOD FOR DIAGNOSING VISION DISORDERS

BACKGROUND OF THE INVENTION

1. Field of the Invention

The invention relates to apparatus and methods for comparing and correlating disparate types of data and providing a combined presentation of the data to aid in the diagnosis of biological disorders.

2. Background of the Related Art

Frequently medical doctors and technicians attempt to diagnosis a biological disorder of a patient using the results of several different types of tests. This often requires that two or more disparate types of data be correlated and/or compared to one another to determine the cause of a biological disorder or condition. Correlating and/or comparing the disparate types of data can be difficult and time consuming because the disparate types of data are often presented in different formats or in different orientations.

For instance, when a doctor is attempting to determine why a patient has lost some degree of vision sensitivity, he will usually begin by conducting a perimetry test, which determines which areas within a patient's visual field have experienced a loss of sensitivity. The doctor will then attempt to match up a loss of vision sensitivity to a specific eye disorder or biological defect. The eye disorder or biological defect must be determined by examining the biological structures responsible for vision using some sort of testing device. The doctor must then compare and correlate the perimetry data to the data on the biological structures to determine whether a defect or condition of a biological structure is responsible for a measured loss of vision. This comparison is often difficult because of the very different ways that perimetry data and biological structure data are presented, as will be explained below.

Perimetry testing, which measures the sensitivity of a patient's eye, can be done many different ways. The results of a perimetry test are presented on a chart that is indicates the sensitivity of one or more eyes at different positions within the eye's visual field. Regardless of the method used, the results are usually presented in one of two different formats.

The results of a perimetry test are shown in a first format in FIG. 1. A plurality of concentric isopter lines 22, 24, 26, 29 are drawn on the chart to indicate the eye's sensitivity. Each isopter line connects points within the patient's visual field having substantially the same sensitivity. The isopter line 22 corresponds to the lowest visual sensitivity, whereas isopter line 29 corresponds to the greatest optical sensitivity. The isopter lines provide a map of how the sensitivity of the patient's vision changes within the field of view.

As can be noted from the chart 20 in FIG. 1, the sensitivity of a person's vision does not vary in a simple proportional manner as one progresses from the center of the line of vision outward towards the fringes of the patient's peripheral vision. In addition, because of the structure of the human eye, a patient's field of vision through an individual eye will always include a blind spot 28 located to the temporal side of the central line of vision. The blind spot 28 corresponds to the point on a person's retina at which the optic nerve is attached.

Perimetry testing is performed on each of a patient's eyes, individually. A chart such as the one shown in FIG. 1 represents the sensitivity of a person's vision through a single eye. However, it is common to present the results of perimetry testing in a chart such as the one shown in FIG. 2, which shows the sensitivity of a person's vision in both the left and the right eyes.

The chart shown in FIG. 2 is arranged such that the left hand side of the chart corresponds to the patient's vision through his left eye and the right side of the chart corresponds to the patient's vision through his right eye. This orientation is referred to as a "patient's view" orientation. This means that the information corresponding to the left and right eyes are oriented on the page such that they correspond to how a patient would see out into the world.

Perimetry data is presented in a different format in the chart shown in FIG. 3. This chart, which includes a plurality of numbers arranged on perpendicular axes, also indicates a patient's visual sensitivity at different positions within the visual field. The greater the number, the greater the patient's sensitivity at a particular location. The perimetry chart in FIG. 3, like the one in FIG. 2, is arranged in a "patient view" orientation, where the left side represents the visual sensitivity of the patient's left eye and the right side represents the visual sensitivity of the patient's right eye.

As can be seen for the left eye in the chart of FIG. 3, the numerals towards the center of the patient's vision are in the low to mid 30's while the numerals at the edge of the person's vision tend to be in the mid 20's. This indicates that the patient's vision is more sensitive toward the center of his field of vision, and less sensitive toward the edges of his field of view.

Perimetry charts such as the ones shown in FIGS. 2 and 3 indicate the sensitivity of photo-receptors located on the retina of a patient's eye. For a single eye, the sensitivity indicated on the left side of a perimetry chart actually corresponds to photo-receptors located on the right side of the retina. Similarly, the sensitivities indicated on the top of a perimetry chart correspond to photo-receptors located on the bottom of the retina. The inversion of the sensitivity information relative to the location of the photo-receptors is caused by the lens of the eye, which inverts images that pass through the lens. FIG. 4 is a diagram helpful in understanding the inversion of images. The lens 70 of an eye will invert an image 74 as the image is focused on the retina of the eye. The focused image 72 is upside down and is reversed from left to right relative to the original image 74.

A doctor examining a patient's eye will typically look into the patient's eye using a magnifying device to conduct a visual examination of the transparent structures of the eye. To accomplish this examination, light from an instrument is typically beamed into a person's eye, and the light reflects off the structures of the eye, back through the lens 70 of the eye, towards the doctor. Because of the eye's lens 70, the image of the structures leaving the patient's eye is inverted with respect to the location of the actual structures. Some devices that allow a doctor to perform such an examination will simply magnify the image that passes through the lens. Thus, the doctor is viewing an inverted image of the eye structure. Other devices that allow a doctor to conduct such an examination will automatically invert the image that emerged from the lens so that the image of the structures seen by the doctor are correctly oriented relative to the actual structures.

An image of the visible structures of an eye is typically called a fundus image. An example of a fundus image is shown in FIG. 5. A fundus image will usually show the retina of the eye and visible blood vessels. The point at which the optic nerve attaches to the retina usually appears as a lighter area in the image. A portion of the eye called the macula (which corresponds to the center of an eye's field of vision) will usually appear as a darker area in the image.

There are several different types of devices which can record a fundus image of the visible structures of an eye. These devices can record a photographic image of an eye's structure, or they can utilize a charge coupled device to record electronic data corresponding to an image of the eye's structure.

When fundus images of a person's eye are presented, they are typically presented as shown in FIG. 6. The right eye is typically shown on the left hand side of the page, while the left eye is shown on the right hand side of the page. This orientation is called the "doctor view" orientation. Because the devices that obtain fundus images of a person's eye will typically automatically invert the image that passes through the lens of an eye, structures shown at the top of a fundus image correspond to structures actually located at the top of the eye. Similarly, structures appearing on the right hand side of the fundus image correspond to structures actually located on the right side of the eye.

Unfortunately, a doctor may find it difficult to correlate a loss of vision shown in perimetry chart, such as the ones shown in FIGS. 2 and 3, with the structures shown in a fundus image, such as the one shown in FIG. 6, due to the orientations of the information appearing on a perimetry chart and orientations of the eye structure shown in a fundus image. This difficulty is caused by the presentation of perimetry data in a "patient view" orientation and the presentation of fundus images in a "doctor view" format. The relative positions of the left and right eyes in a fundus image are reversed with respect to the positions of the left and right eyes on a perimetry chart. In addition, due to the inverting effect of the eye's lens, a loss of vision sensitivity indicated at the top portion of a perimetry chart actually corresponds to a loss of sensory ability of the structures located at the bottom of a person's eye. Thus, the information shown in a perimetry chart is actually inverted top-to-bottom and left-to-right with respect to the structures shown in a fundus image. Because the orientation of the data on a perimetry chart is inverted with respect to the structures shown in a fundus image, a doctor can have difficulty relating the information in a perimetry chart to the structures shown in a fundus image. This makes the diagnosis of eye vision disorders difficult and time consuming.

The same types of problems are encountered when other disparate types of test data must be correlated to diagnose a biological disorder or condition.

SUMMARY OF THE INVENTION

The invention is an apparatus and method for correlating disparate types of information derived from testing and for providing a combined presentation of the data. A system or method embodying the invention automatically compares one type of data to at least one other disparate type of data, and combines the data so that the disparate data can be presented together. A system or method embodying the invention makes it easier and quicker for a doctor or medical technician to diagnose the cause of a biological disorder or condition using the combined presentation of the data.

In one embodiment of the invention, optical sensitivity data may be combined with data regarding a patient's biological structures responsible for vision. The combined data is presented in a manner that makes it easier for a doctor to diagnose the cause of a loss of vision sensitivity. A device or method embodying the invention may be capable of automatically correlating a loss of vision to a specific biological structural defect or condition to identify the cause of the loss of vision.

In an embodiment of the invention, perimetry data taken from a perimetry test is superimposed on a fundus image. It will generally be necessary to invert either the perimetry data or the fundus image to ensure that the sensitivity information reflected in the perimetry data is superimposed onto corresponding structures shown in the fundus image. Also, if data from both eyes is presented in the combined image, the position of the left and right eyes on the page must be reversed in either the perimetry data or the fundus image since the perimetry data appears in a patient view orientation and the fundus images appear in a doctor view orientation.

An example of such a combined image is shown in FIG. 7. The numerals from a perimetry test are superimposed onto a fundus image at the locations of the structures giving rise to the indicated sensitivities. For instance, the perimetry numeral corresponding to the attachment point of the optic nerve 92 is 0, which indicates the patient's blind spot. The numerals surrounding the macula 94 of the eye are greatest, indicating the highest optical sensitivity. The numerals around the exterior edges of the eye are lower, indicating a decreased optical sensitivity. Another example of a combined image of perimetry data (presented in isopter lines) and a fundus image is shown in FIG. 8. In FIG. 8, isopter lines 96 test are superimposed onto a fundus image of a person's eye.

In other embodiments of the invention, any type of optical sensitivity or acuity data may be superimposed onto data reflective of a biological structure responsible for vision. Typically, the structure data will be an image of a biological structure of a patient responsible for vision. However, any type of structure data could be used. For instance, perimetry data may be superimposed onto an image of a person's optic nerve or a portion of a person's brain responsible for processing vision information, each of which may be obtained through magnetic resonance imaging. Similarly, structure data could be obtained using an infrared test device, an ultrasound test device, a thermal imager, or any other type of test device. Optical sensitivity data could also be superimposed onto an image of the exterior of an eye and its associated eyelid.

In still other embodiments of the invention, individual images of biological structures are stored in separate "structure data layers." Optical sensitivity data is stored in a "sensitivity data layer." Pattern recognition processes are then conducted on each data layer to identify specific patterns in the data. Next, pattern matching between the sensitivity data layer and the structure data layers is conducted to correlate identified patterns in the sensitivity data layer to identified patterns in the structure data layers. This allows large amounts of data to be processed by a computer to rapidly correlate a vision loss to a specific defect or condition of a biological structure that is causing the vision loss.

A device and method embodying the invention, where optical sensitivity data is automatically related to portions of biological structures responsible for vision, makes it easy for a doctor to identify specific structural problems and defects that are causing a loss of vision.

In still other embodiments of the invention, any type of test data could be correlated with any other disparate type of test data to create a combined presentation of the test data to make a medical diagnosis easier and quicker. Similarly, a first type of test data could be correlated and compared to multiple different disparate types of test data using a pattern recognition and matching process, such as the one described above.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

Embodiments of the present invention will be described in conjunction with the following drawings, wherein like elements are identified with like reference numbers, and wherein:

FIG. 3 is a chart showing the results of a perimetry test on a patient's left and right eyes;

DETAILED DESCRIPTION OF PREFERRED EMBODIMENTS

Figure 9:
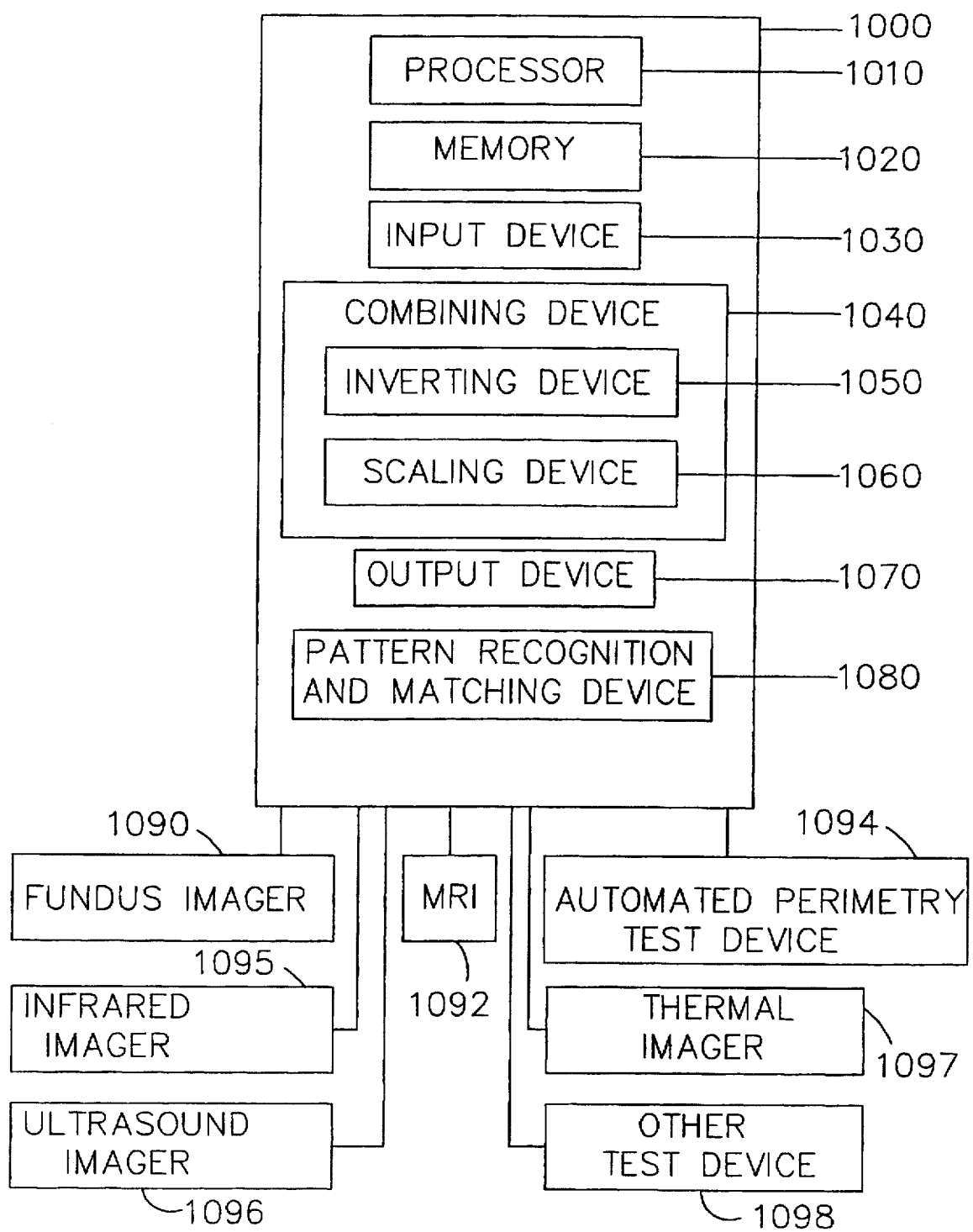
FIG. 9 is a diagram showing the elements of a device embodying the invention.

A diagram of a device embodying the invention is shown in FIG. 9. The device 1000 includes a processor 1010 for processing disparate types of data, a memory 1020, an input device 1030, a combining device 1040, an output device 1070 and a pattern recognition and matching device 1080. The combining device 1040 includes an inverting device 1050 and a scaling device 1060.

Figure 1:
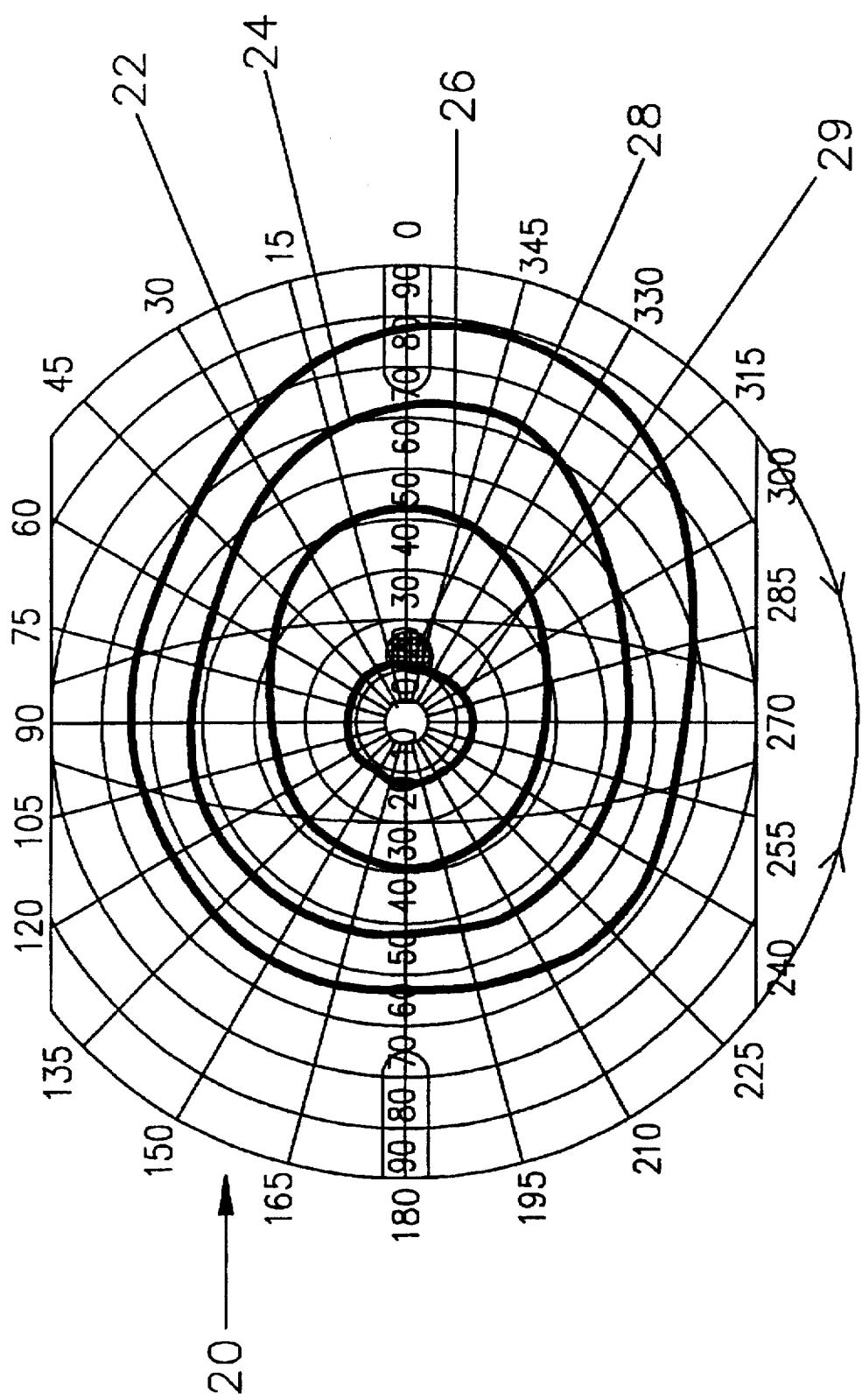
FIG. 1 is a chart showing the results of a perimetry test on a patient's eye.
Figure 2:
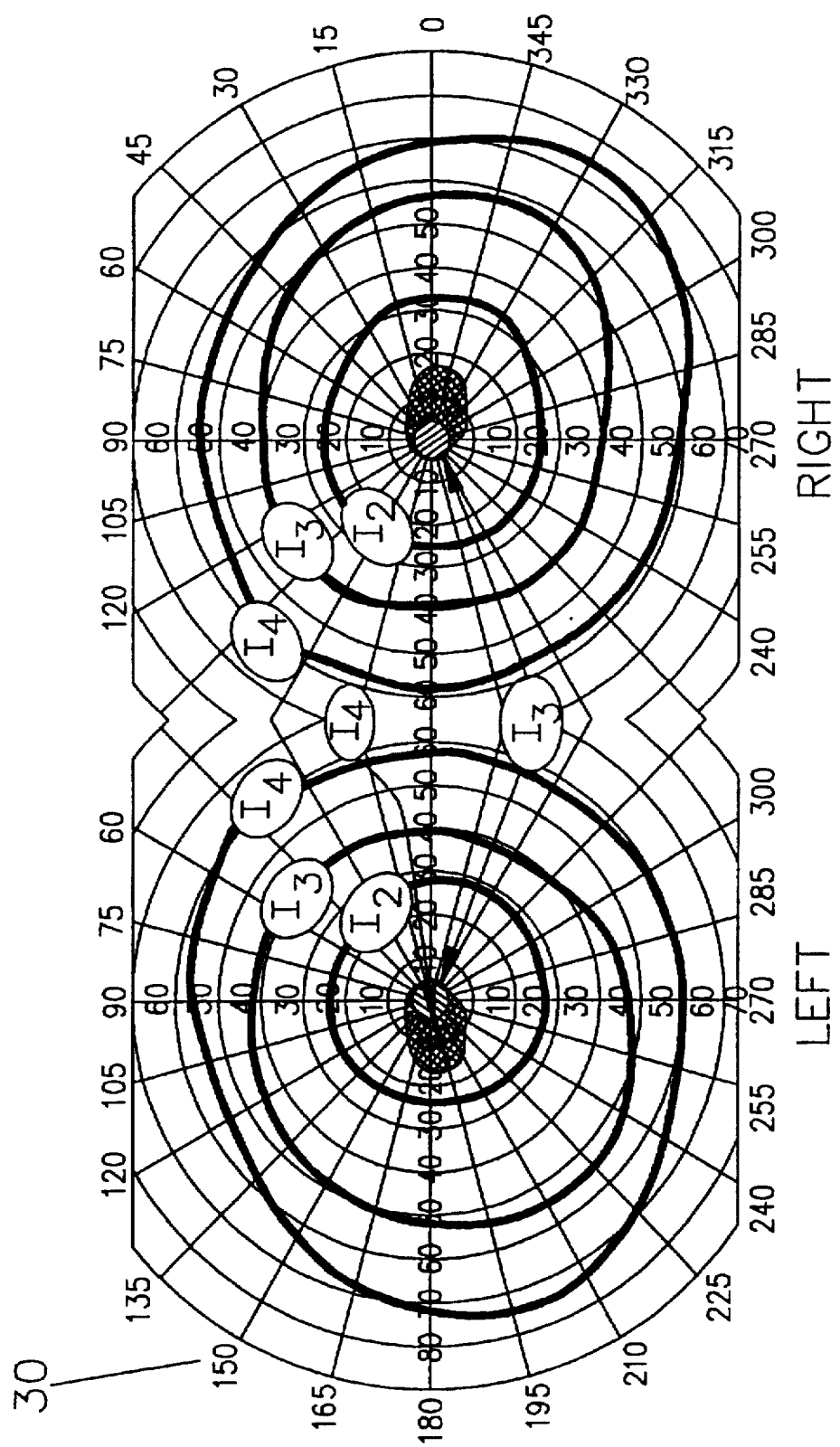
FIG. 2 is a chart showing the results of a perimetry test on a patient's left and right eyes.
Figure 3:
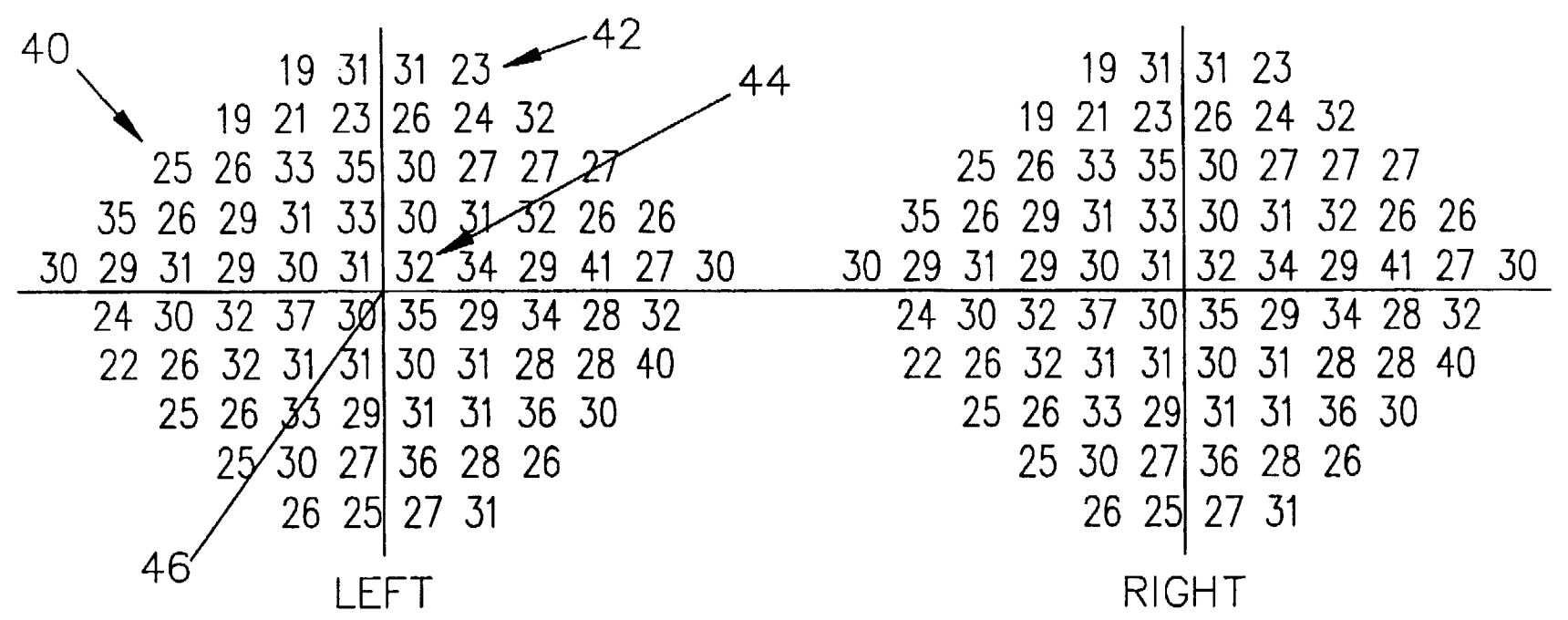
Figure 4:
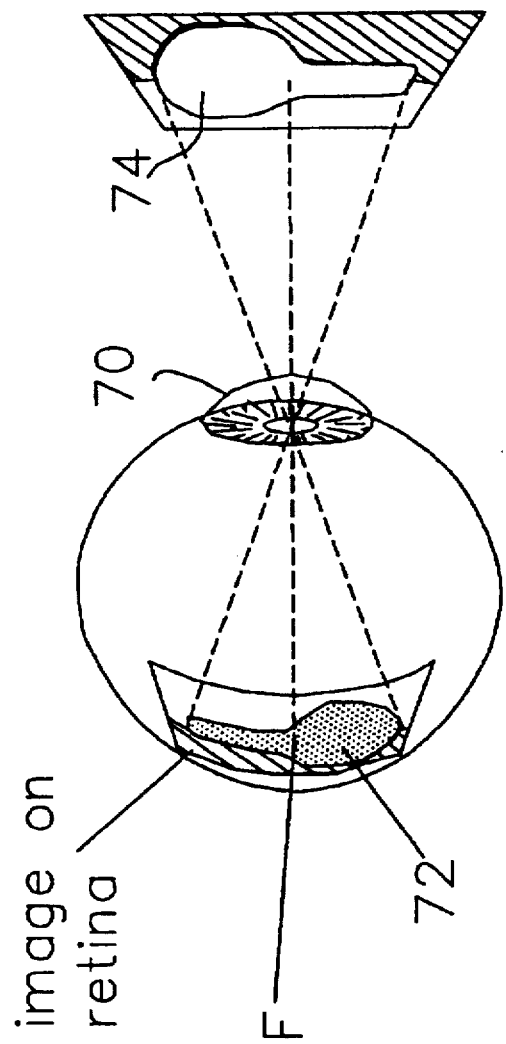
FIG. 4 is a diagram showing how images are inverted when passing through the lens of an eye.
Figure 5:
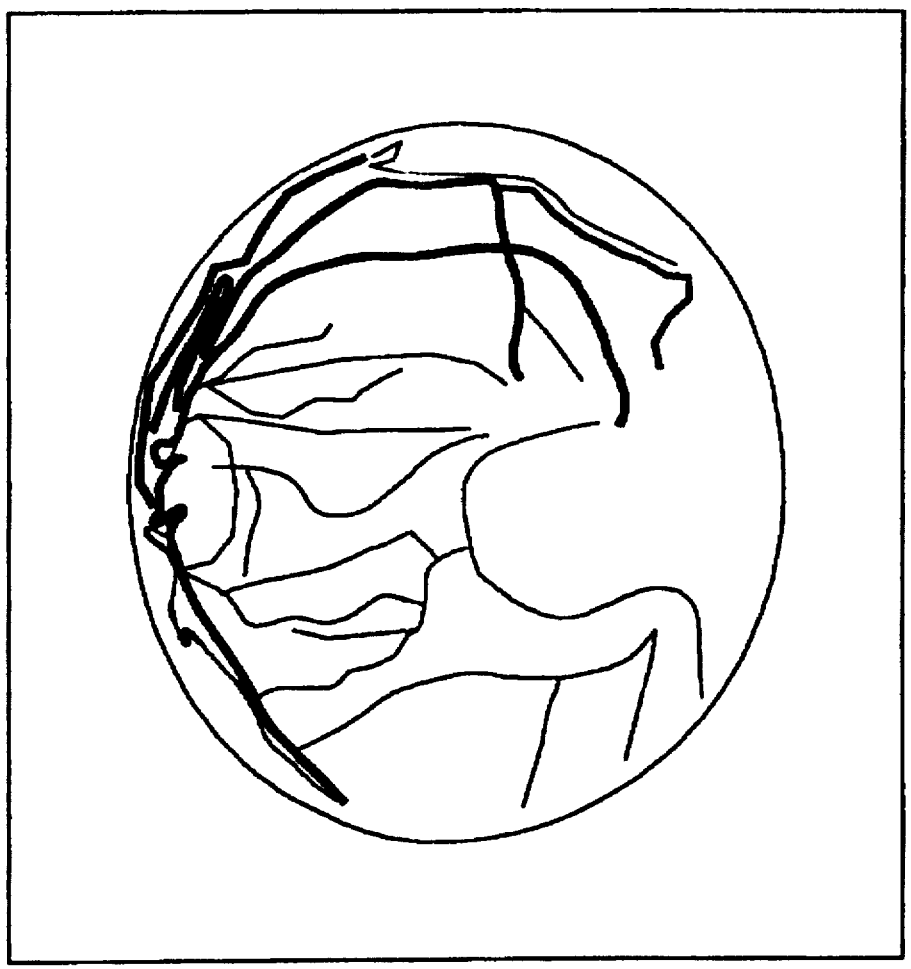
FIG. 5 is a fundus image of an eye.
Figure 6:
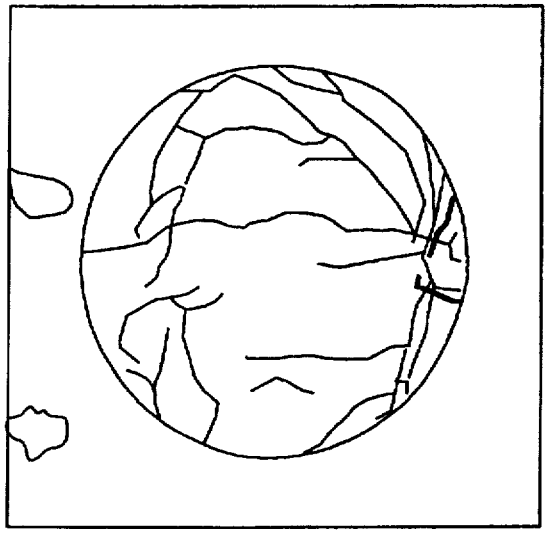
FIG. 6 shows fundus images of a patient's right and left eyes.
Figure 6:
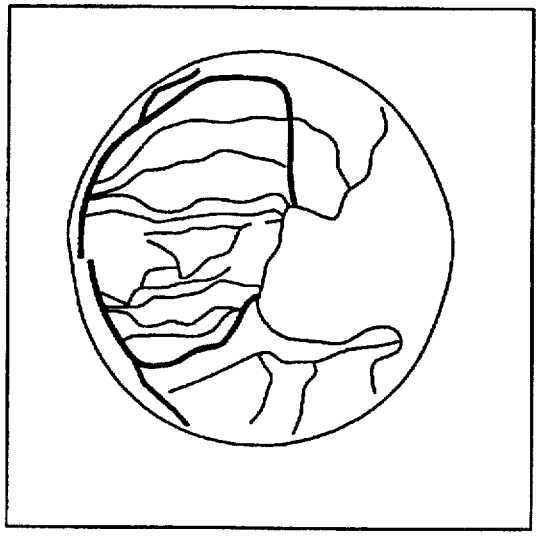

In a first embodiment of the invention, optical sensitivity data in the form of perimetry data is correlated to a fundus image of an eye. In the first embodiment, the processor 1010 and the memory 1020 could be part of a typical microcomputer or personal computer. Perimetry data regarding the optical sensitivity of a patient's eye is first input to the device 1000 via an input device 1030. The perimetry data may be in the form of isopter lines or numerals indicative of optical sensitivities. The perimetry data may be input in the form of one or more data files, in which case the input device 1030 could simply be a data input port of a computer, or a magnetic or optical disk reader. Alternatively, the perimetry data could be input by scanning an image of a perimetry chart, such as the ones shown in FIGS. 1, 2 and 3. When a perimetry chart is scanned, the data input device 1030 could comprise a scanner and appropriate software capable of converting a scanned image of a perimetry chart into data that can be used by the processor 1010.

Next, fundus images of the patient's eyes are input to the device 1000 via the input device 1030. The fundus images could be input as one or more data files from a separate fundus imager 1090, or the fundus images could be scanned from images produced by a fundus imager. As noted above, the input device 1030 could comprise a data input port of a computer, a magnetic or optical disk reader, or a scanner and appropriate software for converting a scanned image into data usable by the processor 1010. In yet other embodiments of the invention, the input device 1030 could comprise a device for obtaining an image of a patient's eyes, such as a charge coupled device, and for converting the image into data usable by the processor 1010.

The combining device 1040 then combines the perimetry data and the fundus image data to create a combined image wherein the perimetry data is superimposed onto the structures in the fundus images giving rise to the indicated optical sensitivities. A user may be able to choose either the patient view or doctor view orientations for the combined image. Because perimetry data is usually presented in a patient-view format, if a user selects a doctor view orientation for the output, it will usually be necessary to invert the perimetry data with the inverting device 1050 in order for the optical sensitivities represented in the perimetry data to align with the structures shown in the fundus image. Conversely, if a user selects the patient view orientation for the output, it will usually be necessary to invert the fundus image so that the perimetry data can be superimposed on the appropriate structures in the fundus image, and so that the combined image will be in the patient view orientation. Also, if the perimetry data and fundus images are for both eyes of a patient, it will usually be necessary to reverse the orientation of either the perimetry data or the fundus images so that the output is placed in the selected orientation. The inverting device 1050 may comprise a computer program that is run by the processor 1010.

Also, if the scale of the perimetry data does not match the scale of the fundus image, it will be necessary to scale either the perimetry data or the fundus image so that their sizes match and the perimetry data may be superimposed on the appropriate structures shown in the fundus image. Scaling the perimetry data to match the fundus image can be accomplished using the scaling device 1060 of the combining device 1040. The scaling device 1060 may also comprise software that is run by the processor 1010.

In one embodiment of the invention, the scaling device 1060 selects reference points in both the perimetry data and the fundus image, and either the perimetry data or the fundus image are enlarged or reduced until the reference points coincide. For instance, in the fundus image, the location of the attachment point of the optic nerve can be identified as a lighter portion of the image, and the location of the macula can be identified as a relatively dark area within the fundus image. In the perimetry data, these two locations correspond, respectively, to the blind spot where optical sensitivity is zero, and the central portion of the field of vision where optical sensitivity is highest. The scaling device 1060 may be a computer program run by the processor 1010 that identifies these reference points in the perimetry data and the fundus image, and then alters the scale of either or both the fundus image and the perimetry data until the reference points coincide in a combined image.

Figure 7:
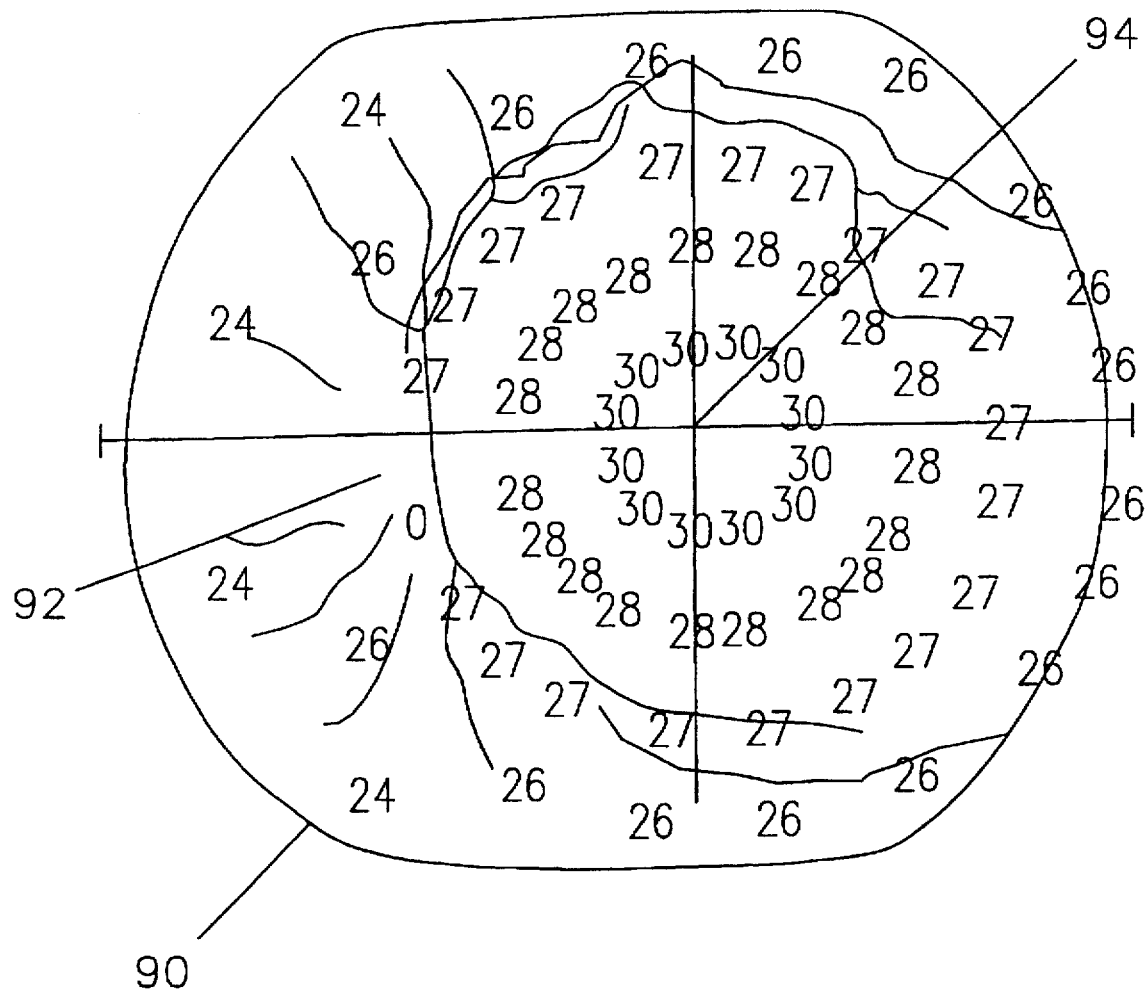
FIG. 7 is a combined image of perimetry data and the fundus of an eye.
Figure 8:
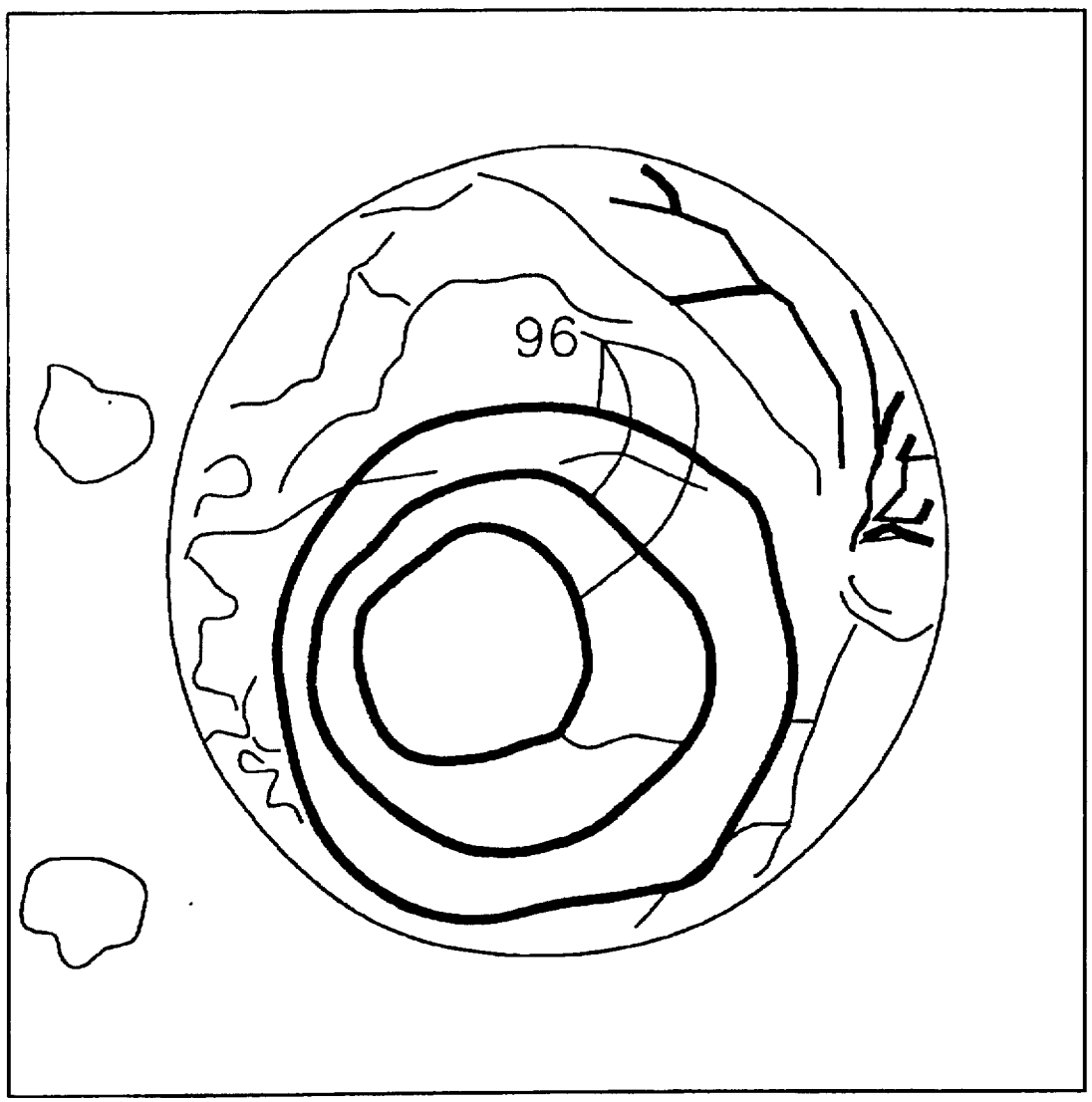
FIG. 8 is a combined image of perimetry data and the fundus of an eye.

After the combining device creates a combined image of the perimetry data and the fundus image, the output device 1070 outputs the combined image, which can then be examined by a doctor to aid in the diagnosis of vision defects. Examples of a combined image of perimetry data and a fundus image are shown in FIGS. 7 and 8. Although FIGS. 7 and 8 show a combined image for only a single eye, the device 1000 could create combined images for both the left and right eyes of a patient, and the combined images could be presented in a single printout in either the patient view or doctor view formats.

The output device 1070 could comprise a computer screen upon which the combined image is displayed, a printer that prints the combined image, a photographic device that creates a negative or photographic print of the combined image, or a projector that displays the combined image on a large screen. Alternatively, the output device 1070 could comprise any other device capable of displaying the combined image to a user. For instance, should three dimensional holographic projectors become available in the future, such a device would be ideal for presenting a user with a combined three dimensional image of the perimetry data and fundus image.

Other embodiments of the invention could combine perimetry data with images of other structures of a patient responsible for vision. For instance, a device embodying the invention might combine perimetry data with an image of an optic nerve or an image of a portion of a patient's brain responsible for vision taken through magnetic resonance imaging (MRI) or other means. In an embodiment using an image of an optic nerve, the combining device 1040 would manipulate the input optic nerve image data and/or the perimetry data such that the perimetry data is superimposed on corresponding portions of the optic nerve image.

In yet another embodiment of the invention, the optical structure data may comprise an image of the exterior of an eye and its associated eyelid. Some medical conditions cause the eyelid of a person's eye to droop over the eye, thus obscuring a portion of the person's field of vision. By combining an image of an exterior of an eye and the associated eyelid with perimetry data from a perimetry test, one can determine whether the drooping of the eyelid gives rise to a measurable loss of vision.

Other embodiments of the invention could create combined images showing perimetry data superimposed onto an image of any other biological structure responsible for vision. Also, although the figures show the perimetry data represented as numerals or isopter lines, the perimetry data could also be represented by any type of user recognizable symbol or pattern that is indicative of the sensitivity of the patient's eye.

In yet other embodiments of the invention, images of biological structures responsible for vision could be combined with optical sensitivity or acuity data other than perimetry data. Any type of optical sensitivity or acuity data could be correlated to biological structures by a device or method embodying the invention to aid a doctor in diagnosing vision disorders.

In still other embodiments, data indicative of a biological structure responsible for vision, other than image data, may be correlated to optical sensitivity data. Although image data is described for many of the embodiments, any type of structure data could be used. For instance, images or structure data may be obtained by an ultrasound imager 1096, an infrared imager 1095, a thermal imager 1097, another type of electromagnetic radiation testing device, or any other type of test device 1098.

In addition, the principles of the invention are not limited to correlating optical sensitivity data to biological structure data. A device or method embodying the invention could be used to combine any two or more disparate types of data obtained through any testing devices. As mentioned above, it is quite common for a doctor or medical technician to correlate the results of disparate tests in attempting to diagnose a biological disorder or condition. A device embodying the invention and incorporating a pattern recognition and matching device could be used to correlate the results or any disparate tests, as will be explained below.

A device embodying the invention and including a pattern recognition and matching device 1080 could be used to correlate vision sensitivity or acuity data, such as perimetry data, with data regarding a biological structure responsible for vision. For instance, in an embodiment of the invention employing a pattern recognition and matching device 1080, perimetry data could be compared to multiple images of a patient's brain responsible for processing vision information. Each of the plurality of images of the patient's brain, which could be separate scanned slices of the brain taken with a magnetic resonance imager or other image generating device, would be stored in a separate "structure data layer." Each structure data layer could comprise a digital data file corresponding to an image of the brain. The perimetry data could also be stored in a "perimetry data layer," which could also comprise a digital data file corresponding to a perimetry data chart.

Once the structure data layers and the perimetry data layer have been created, the device 1000 would carry out a pattern recognition process utilizing the pattern recognition and matching device 1080. In the pattern recognition process, each of the data layers would be examined in turn, in an attempt to identify patterns appearing in the data. Once patterns have been identified in each of the data layers, the pattern recognition and matching device 1080 would attempt to match up identified patterns in the perimetry data layer with corresponding patterns appearing in one or more of the structure data layers. The device could thus rapidly identify a correlation between a loss of vision, as reflected in the perimetry data, and a structural defect or condition that can be discerned in the magnetic resonance images of the brain.

A similar pattern recognition process could be carried out with structural data regarding any portion of a biological structure of a patient responsible for processing vision, such as an optic nerve, or structures within a person's eye. Also, such a pattern recognition process could be conducted with any type of visual sensitivity or acuity data, not just perimetry data. Further, the pattern recognition and matching device could be used to compare and correlate any two or more disparate types of data to aid a doctor in arriving at a diagnosis. This process is not limited to vision disorders.

As shown in FIG. 9, a device 1000 embodying the invention may be directly connected to a fundus imager 1090, a magnetic resonance imager 1092, an automated perimetry test device 1094, an infrared imager 1095, an ultrasound imager 1096, a thermal imager 1097 or any other type of test device 1098 so that information can be easily exchanged between the devices. When the device 1000 is connected to one or more of these elements, the device would be capable of automatically testing a patient and correlating the test data in an attempt to determine the cause of a biological defect or condition.

Figure 10:
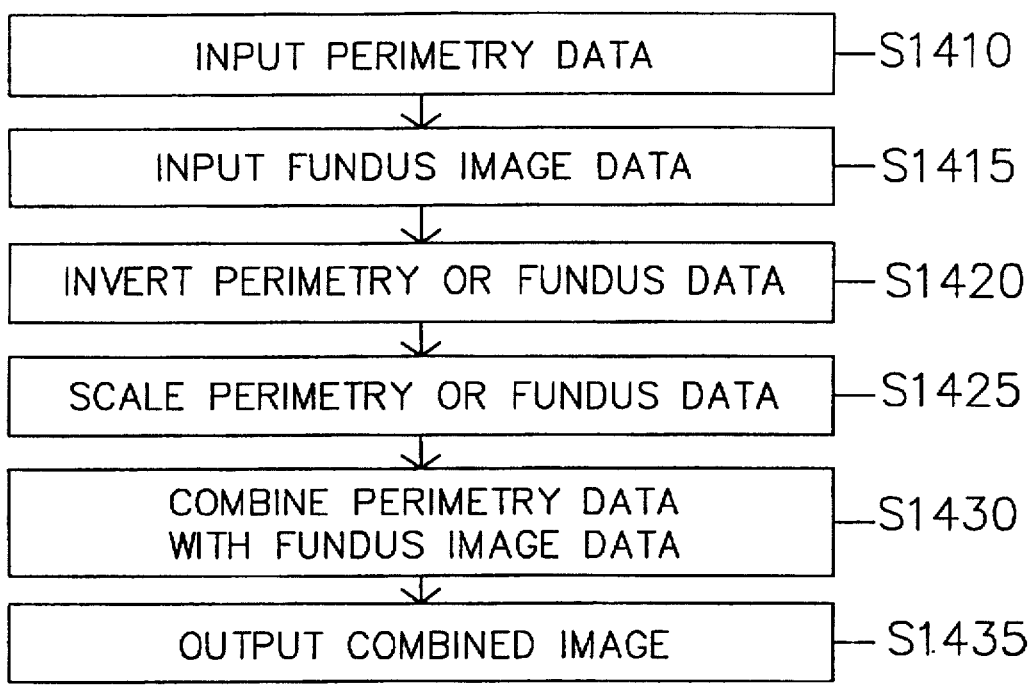
FIG. 10 is a flow chart showing the steps of a method embodying the invention.

A method embodying the invention is shown in FIG. 10. In this method, perimetry data and fundus image data are input to a device and the device creates a combined image where the perimetry data is superimposed on the fundus image. Although this example is related to comparing and correlating vision information, a similar process could be used to correlate any two disparate types of data to create a combined presentation of the data that would aid a doctor in arriving at a diagnosis.

In a first step 1410, perimetry data is input to a device. The perimetry data could be input in the form of one or more data files, or perimetry charts could be scanned. In step 1415, a fundus image is input. The fundus image could also be input as a data file, or a fundus image could be scanned. In yet another embodiment, data from a charge coupled device focused on an eye could be directly input in either an analog or digital form. The fundus image could also be input using any other sort of data input device or scanner capable of inputting data representative of the fundus image.

In step 1420, either the perimetry data or the fundus image are inverted. Typically, a user would select either the doctor view or patient view orientation for the combined presentation. If the patient view orientation is selected, the fundus image (which is usually in the doctor view orientation) would be inverted. If the doctor view orientation is selected, the perimetry data (which is in the patient view orientation) would be inverted.

In step 1425, either the perimetry data or the fundus image, or both, are scaled so that the perimetry data can be superimposed on the fundus image such that the perimetry data overlies corresponding structures in the fundus image. The scaling step could be performed as described above, wherein two reference points are determined on both the perimetry data and the fundus image, and the scale of either or both of the perimetry data and the fundus image is altered until the reference points coincide.

In step 1430, the perimetry data is combined with the fundus image data to create a combined image. Finally, in step 1435, the combined image is output. The combined image may be output using a printer, a plotter, or the combined image may be displayed on a computer or projection screen. Any type of output device capable of creating or displaying the combined image could be used to perform the output step.

A method embodying the invention and similar to the one described above could also be used to create combined images of any type of optical sensitivity or acuity data with structural data regarding any biological structure responsible for vision. For instance, visual sensitivity data could be combined with an image of the exterior of an eye and its associated eyelid, an image of an optic nerve, or an image of a portion of a brain responsible for processing vision information. In addition, such a method could be used to combine and correlate any two disparate types of data to create a combined presentation of data, the data need not relate to vision. Also, the output step might further comprise altering the combined image to present the combined image in a patient view or a doctor view format.

Figure 11:
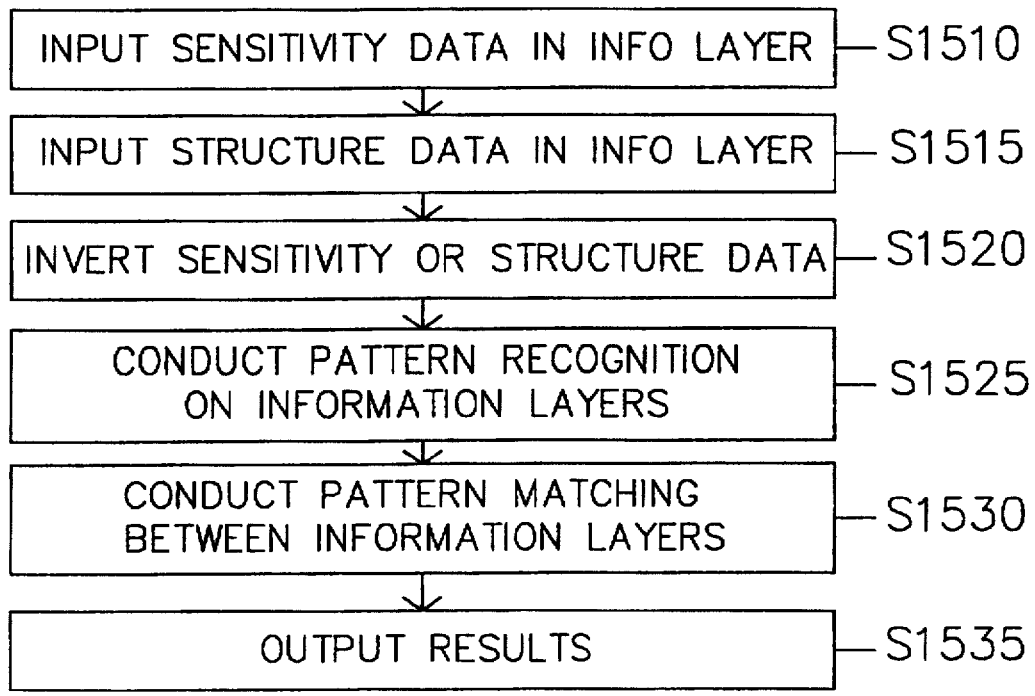
FIG. 11 is another flow chart showing the steps of another method embodying the invention.

Another method embodying the invention is shown in FIG. 11. In this method, optical sensitivity data and optical structure data are stored in data layers, and a pattern matching process is performed to identify defects or conditions of a patient's biological structures that correlate to a loss of vision sensitivity, as reflected in the sensitivity data. Although this process is described in conjunction with optical sensitivity and structure data, any two type of disparate data could be compared to one another using this method in an attempt to correlate patterns in the data.

In a first step 1510, vision sensitivity data, such as perimetry data, is input to a sensitivity data layer. The vision sensitivity data may be input in the form of data files, or it may be scanned from a perimetry chart. In step 1515, structural data is input into at least one structure information data layer. If multiple images of a biological structure responsible for vision are obtained, each of the images may be stored in a different structure information data layer.

In step 1520, either the sensitivity data layer or the structure data layer is inverted so that the orientations of each of the data layers is the same. This step may not be necessary if the input data is already in the same orientation. Also, if a user selects an output orientation for the data, this may determine which of the data layers is inverted, as described above in connection with the method shown in FIG. 10.

In step 1525, a pattern recognition process is performed to identify one or more patterns in each of the data layers. In step 1530, any patterns identified in the sensitivity data layer are compared to patterns identified in the structure data layers. An attempt is made to match the identified patterns to correlate a defect or condition of the biological structure with a variation of vision sensitivity, as noted in the sensitivity data. In step 1535, the results of the pattern matching step are output. The results may be output in the form of a report, or in the form of a combined presentation of the two types of data. For instance, a combined image which superimposes perimetry data on at least one image of a biological structure may be output.

Although the method described above utilizes vision sensitivity data and biological structure data, other methods embodying the invention could compare any two or more disparate types of data.

A process embodying the invention, such as the one described above in connection with FIG. 11, could be used to rapidly compare perimetry data, or any other type of visual sensitivity or acuity information, to each of a large number of images of a biological structure responsible for vision. The method could be used to automatically identify a defect or condition of a biological structure which gives rise to a loss of vision.

It is to be understood that the foregoing embodiments are merely illustrative. Numerous variations, modifications and changes could be made to the above described embodiments without departing from the scope and spirit of the invention, as defined in the following claims.

What is claimed is:

1. A device for combining optical data, comprising:
   means for combining optical sensitivity data with optical structure data to create a combined set of data; and
   means for outputting the combined set of data.

2. The device of claim 1, wherein the optical structure data comprises a fundus image, and wherein the combined set of data comprises optical sensitivity data superimposed on the fundus image.

3. The device of claim 2, wherein the combined set of data comprises isopter lines that are superimposed on the fundus image.

4. The device of claim 2, wherein the combined set of data comprises symbols indicative of optical sensitivity that are superimposed on the fundus image.

5. The device of claim 1, wherein the optical structure data comprises a magnetic resonance image of one of a portion of an optic nerve and a portion of a brain responsible for vision, and wherein the combined set of data comprises optical sensitivity data superimposed on the magnetic resonance image.

6. The device of claim 5, wherein the combined set of data comprises isopter lines that are superimposed on the magnetic resonance image.

7. The device of claim 5, wherein the combined set of data comprises symbols indicative of optical sensitivity that are superimposed on the magnetic resonance image.

8. The device of claim 1, wherein the optical structure data comprises an image of the exterior of an eye and its associated eyelid, and wherein the combined set of data comprises optical sensitivity data that is superimposed on the image of the exterior of an eye and its associated eyelid.

9. The device of claim 8, wherein the combined set of data comprises isopter lines that are superimposed on the image of the exterior of an eye and its associated eyelid.

10. The device of claim 8, wherein the combined set of data comprises symbols indicative of optical sensitivity that are superimposed on the image of the exterior of an eye and its associated eyelid.

11. The device of claim 1, wherein the combining means comprises means for inverting one of the optical sensitivity data and the optical structure data.

12. The device of claim 1, wherein the combining means comprises means for scaling one of the optical sensitivity data and the optical structure data.

13. The device of claim 1, wherein the output means comprises means for outputting the combined set of data in one of a patient view format and a doctor view format.

14. The device of claim 1, further comprising means for recognizing patterns in the optical sensitivity data and the optical structure data.

15. The device of claim 14, further comprising means for matching patterns recognized in the optical sensitivity data and the optical structure data.

16. The device of claim 1, further comprising imaging means for capturing, as said optical structure data, an image of one of structures of an eye, an optic nerve, and a portion of a brain responsible for processing optical information.

17. The device of claim 16, wherein the imaging means comprises a photographic device.

18. The device of claim 16, wherein the imaging means comprises a magnetic resonance imager.

19. The device of claim 16, wherein the imaging means comprises a charged coupled device for obtaining electronic data representative of an image.

20. A device for correlating optical sensitivity data to optical structure data, comprising:

means for identifying patterns in optical sensitivity data and optical structure data;

means for matching an identified pattern in the optical sensitivity data to an identified pattern in the optical structure data; and reporting means for reporting pattern matches.

21. The device of claim 20, wherein the reporting means comprises means for combining an image of optical sensitivity data with an image of optical structure data to create a combined image.

22. The device of claim 20, wherein the pattern matching means identifies portions of a biological structure represented by the optical structure data that give rise to a reduced vision sensitivity reflected in the optical sensitivity data.

23. A method of combining optical sensitivity data with optical structure data, comprising the steps of:

obtaining optical sensitivity data indicative of a sensitivity of an eye;

obtaining optical structure data; and combining the optical sensitivity data and the optical structure data to create a combined set of data.

24. The method of claim 23, wherein the step of obtaining optical structure data comprises obtaining an image of a biological structure responsible for vision.

25. The method of claim 24, wherein the combining step comprises combining the obtained optical sensitivity data and the obtained image such that individual portions of the optical sensitivity data are superimposed on portions of the image to which they correspond.

26. The method of claim 23, wherein the step of obtaining optical structure data comprises obtaining an image of one of a structure of an eye, a portion of an optic nerve and a portion of a brain responsible for vision.

27. The method of claim 23, wherein the combining step comprises superimposing the obtained optical sensitivity data on the obtained optical structure data.

28. The method of claim 23, wherein the combining step comprises superimposing isopter lines on corresponding portions of the obtained optical structure data.

29. The method of claim 23, wherein the combining step comprises superimposing symbols indicative of optical sensitivity on corresponding portions of the obtained optical structure data.

30. The method of claim 23, wherein the combining step comprises inverting one of the obtained optical sensitivity data and the obtained optical structure data.

31. The method of claim 23, wherein the combining step comprises scaling one of the obtained optical sensitivity data and the obtained optical structure data.

32. The method of claim 31, wherein scaling one of the obtained optical sensitivity data and the obtained optical structure data comprises the steps of:

selecting at least two reference points in each of the optical sensitivity data and the optical structure data; and varying the scale of one of the optical sensitivity data and optical structure data until the reference points coincide.

33. A method of combining optical data, comprising the steps of:

combining optical sensitivity data with optical structure data to create a combined set of data; and outputting the combined set of data.

34. The method of claim 33, wherein the combining step comprises combining optical sensitivity data with an image of an optical structure responsible for vision.

35. The method of claim 34, wherein the combining step comprises superimposing the optical sensitivity data on corresponding portions of the image of an optical structure responsible for vision.

36. A method of correlating optical sensitivity data to optical structure data, comprising the steps of:

identifying patterns in optical sensitivity data and optical structure data; and matching an identified pattern in the optical sensitivity data to an identified pattern in the optical structure data; and reporting pattern matches.

37. A method of correlating optical sensitivity data to optical structure data, comprising the steps of:

storing optical sensitivity data for a patient in a sensitivity data layer;

storing optical structure data of the patient in at least one structure data layer;

attempting to match a pattern in the sensitivity data layer to a pattern in the at least one structure data layer; and outputting results of the pattern matching step.

38. The method of claim 37, wherein the pattern matching step comprises the steps of:

identifying at least one pattern in the sensitivity data layer;

identifying at least one pattern in the at least one structure data layer; and attempting to match the at least one identified pattern in the sensitivity data layer to the at least one identified pattern in the at least one structure data layer.

39. The method of claim 37, wherein the step of storing optical structure data in at least one structure data layer comprises storing at least one image of a biological structure of the patient that is responsible for vision in at least one corresponding structure data layer.

40. The method of claim 37, wherein the step of outputting results of the pattern matching step comprises outputting one of a report and an image that identifies a portion of a biological structure of the patient that is responsible for a loss of vision reflected in the optical sensitivity data.

41. A device for correlating optical sensitivity data to optical structure data, comprising:

a processor;

an input device for inputting optical sensitivity data and optical structure data; and a combiner for combining the optical sensitivity data with the optical structure data.

42. The device of claim 41, wherein the combiner comprises an inverter for inverting at least one of the optical sensitivity data and the optical structure data.

43. The device of claim 41, wherein the combiner comprises a scaling device for scaling at least one of the optical sensitivity data and the optical structure data.

44. The device of claim 41, further comprising a pattern recognition device that identifies patterns in the optical sensitivity and optical structure data.

45. The device of claim 44, further comprising a pattern matching device that matches patterns identified in the optical sensitivity data to patterns identified in the optical structure data.

46. The device of claim 41, further comprising an output device for outputting a combined image of the optical sensitivity data and the optical structure data.

47. A device for correlating disparate types of test data, comprising:

means for combining a first type of test data and a second disparate type of test data to create a combined presentation of the first and second types of test data; and means for outputting the combined presentation.

48. A method for correlating disparate types of test data, comprising the steps of:

combining a first type of test data and a second disparate type of test data to create a combined presentation of the first and second types of test data; and outputting the combined presentation.

* * * * *